United States Patent
Guldbaek

(10) Patent No.: US 11,376,394 B2
(45) Date of Patent: Jul. 5, 2022

(54) METHOD OF FORMING A URINARY CATHETER

(71) Applicant: Coloplast A/S, Humlebaek (DK)

(72) Inventor: Teo Kaalund Guldbaek, Dragoer (DK)

(73) Assignee: Coloplast A/S, Humlebaek (DK)

( * ) Notice: Subject to any disclaimer, the term of this patent is extended or adjusted under 35 U.S.C. 154(b) by 425 days.

(21) Appl. No.: 16/613,823

(22) PCT Filed: May 15, 2018

(86) PCT No.: PCT/DK2018/050106
§ 371 (c)(1),
(2) Date: Nov. 15, 2019

(87) PCT Pub. No.: WO2018/210391
PCT Pub. Date: Nov. 22, 2018

(65) Prior Publication Data
US 2020/0179644 A1    Jun. 11, 2020

(30) Foreign Application Priority Data
May 16, 2017    (DK) .......................... PA 2017 70341

(51) Int. Cl.
*A61M 25/00*    (2006.01)
*B29L 31/00*    (2006.01)

(52) U.S. Cl.
CPC .... *A61M 25/0017* (2013.01); *A61M 25/0009* (2013.01); *B29C 2945/7604* (2013.01); *B29C 2945/76006* (2013.01); *B29C 2945/76277* (2013.01); *B29L 2031/7542* (2013.01)

(58) Field of Classification Search
CPC ..... A61M 25/0009; B29C 2945/76006; B29C 2945/7604
See application file for complete search history.

(56) References Cited

U.S. PATENT DOCUMENTS

| | | |
|---|---|---|
| 4,750,877 A | 6/1988 | McFarlane |
| 5,108,689 A | 4/1992 | Uehara et al. |
| 5,240,397 A | 8/1993 | Fay et al. |
| 5,556,582 A | 9/1996 | Kazmer |
| 2016/0263801 A1 | 9/2016 | Zigante et al. |

FOREIGN PATENT DOCUMENTS

| | | |
|---|---|---|
| CN | 1052275 A | 6/1991 |
| EP | 1447200 A2 | 8/2004 |
| EP | 2908998 A1 | 4/2014 |
| FR | 3034318 A1 | 10/2016 |
| FR | 3034342 A1 | 10/2016 |
| JP | 2006205571 A2 | 8/2006 |

(Continued)

*Primary Examiner* — James Sanders
(74) *Attorney, Agent, or Firm* — Coloplast Corp., Coloplast A/S; Nick Baumann

(57) ABSTRACT

A method of forming a urinary catheter is disclosed that includes injecting a polymer melt through a primary melt channel and into an elongated recess around an outer surface of a core; and controlling a first pressure of the polymer melt in a first secondary melt channel separately and individually from a second pressure of the polymer melt in a second secondary melt channel and reducing stress of the polymer melt along the elongated recess. Opening the mould and removing the core provides a moulded intermittent urinary catheter having an open distal end and a closed proximal tip.

11 Claims, 2 Drawing Sheets

(56) References Cited

FOREIGN PATENT DOCUMENTS

| RU | 1831427 | A3 | 7/1993 |
|----|---------|----|--------|
| WO | 9114473 | A1 | 10/1991 |
| WO | 0236324 | A1 | 5/2002 |
| WO | 10149175 | A1 | 12/2010 |
| WO | 13127724 | A1 | 9/2013 |
| WO | 13127725 | A1 | 9/2013 |
| WO | 15198734 | A1 | 12/2015 |

METHOD OF FORMING A URINARY CATHETER

INTRODUCTION

The disclosure relates to the injection moulding of urinary catheters, particularly of the kind having an elongated body extending axially from a distal end to a proximal end and a tip terminating the catheter in the proximal end, and having a conduit extending in the body between an opening in the distal end and an opening in the proximal end, e.g. close to or at the tip.

BACKGROUND

Urinary catheters are widely used by persons who have problems with respect to voluntary emptying of the urinary bladder or persons who need temporary assistance in emptying the urinary bladder. A wide variety of different types of urinary catheters is available to individuals or medical professionals, which are specifically designed for a specific use, such as intermittent catheters or permanent/long term catheters, such as Foley catheters.

Intermittent catheters are widely used by individuals who are paralyzed, such as para- and/or tetraplegics, where the urinary bladder is emptied in regular intervals and the individuals are often capable of inserting the intermittent catheter without assistance. The use of permanent or long-term catheters is usually linked to an individual's hospital stay or at least where the individual is under regular observation of medical professionals, as permanent catheters are not well adapted for self catheterization as they are usually very flexible and have a larger diameter than intermittent catheters and thus are usually inserted by medical professionals under relatively clean or even sterile conditions.

Urinary catheters are generally known to comprise a catheter tube for providing a fluid pathway from the urinary bladder to the outside of the body, a rounded tip for smoothing the insertion of the catheter into the urinary channel and drainage eyes for facilitating the entering of urine into the catheter tube.

The most common method of producing urinary catheters, especially intermittent catheters, is to extrude the catheter tube in a plastic material and subsequently provide the catheter with a tip and drainage eyes. Catheters that are manufactured using the extrusion process have a uniform and constant diameter on both the external and the internal surface from end to end, and therefore have a constant thickness of material throughout the entire length of the catheter tube.

Moulding is a traditional process carried out in different ways. A problem may occur when the moulded article has an extreme shape, e.g. a very long, narrow, or otherwise extraordinary shape. In such cases the melt is difficult to control, and different problems may occur, e.g. non-complete filling of the mould cavity or deformation due to un-even setting of the melt in the mould cavity.

Another problem relates to the core which forms the conduit. The very long and slim shape of the core may cause deformation during moulding and it may potentially be damaged during removal of the moulded catheter from the mould cavity.

SUMMARY

To enable moulding of longer and slimmer catheters, and particularly to enable moulding with long slim internal cavities, to increase productivity, and potentially improve the coherence of the catheter body and tip and thus the quality of the final product, a method and an apparatus according to the independent claims is provided.

Due to the simultaneous injection from both of the at least two secondary melt channels, improved control is facilitated and the method enables the melt from the first of the secondary channels to reach the melt from the other secondary channel inside the mould cavity and thereby facilitate forming of a longer and slimmer urinary catheter. Particularly, the simultaneous injection enables a more homogeneous pressure distribution and thus less stress e.g. on long, slim, core elements which may e.g. form the conduit extending in the body.

The pressure of the melt may be controlled individually in each of the first and second secondary melt channels. Accordingly, the pressure in the first secondary melt channel may be different from the pressure in the second secondary melt channel. This may allow a pressure distribution which ensures complete filling of the mould. The pressure could either be constant during the moulding of a catheter, or the pressure could change during the moulding. If the pressure changes during the moulding of a catheter, the pressure could change individually in the first and second secondary melt channels, e.g. such that only the first, only the second, or both the first and second secondary melt channel change pressure, and the pressure change of the first and the second secondary melt channel, in case they both change, could be identical changes or different changes.

The pressure of the melt may be controlled such that the pressure in at least one of the first and second secondary melt channels exceeds the pressure in the primary channel. In one example, both the first and second secondary melt channel have a higher pressure than the primary melt channel, and in another example one of the first and second secondary melt channels has a higher pressure and the other one has a lower pressure than the primary melt channel.

The temperature of the melt may be controlled individually in each of the first and second secondary melt channels. Accordingly, the temperature of the melt in the first secondary melt channel may be higher or lower than the temperature of the melt in the second secondary melt channel, and the temperature in each of the first and second secondary melt channels may be controlled independent on the temperature in the primary melt channel. The individual temperature control may be used for controlling the viscosity and thus the flowability of the melt in the cavity and/or for controlling where the melt solidifies in the cavity and thus facilitate the correct flow and filling of a long narrow cavity.

The pressure or temperature may be controlled individually without compensation based on pressure or temperature in the mould cavity. Accordingly, the temperature and/or the pressure can be controlled without a feedback from the cavity, e.g. based on a pre-programmed sequence for the temperature and/or pressure. The advantage is that the moulding process may become more robust when the process is controlled without use of sensors. Further, particularly when the moulded article has an extreme shape, e.g. when the article is very long, narrow, or both long and narrow, the control based on a feedback may be difficult due to a relatively large impact on even vary small variations. Accordingly, it may be advantageous to control at least one of the temperature and pressure of the melt, particularly in at least one of the first and the second secondary melt channels, based on static measures and not based on actual conditions in the mould cavity.

Each of the first and second secondary melt channels may be configured to inject melt directly into the mould cavity such that the melt from one of the first and second secondary melt channels only congregate in the mould cavity and not outside the mould cavity. Accordingly, the mixing of the melt occurs exclusively in the mould cavity. This enables a more distinct use of different materials or different handling of identical materials for different areas of the catheter.

The catheter in question could be a urinary catheter for intermittent use or for indwelling use. It could be a relatively short catheter for female use, or it could be a relatively long, i.e. more than 20 cm. long or even more than 25 cm long catheter for male use.

The tip may herein denote a part which is designed for smooth and comfortable insertion into the urethra. Typically, a part designed with well-known characteristics. Examples include Nelaton-tip, Chevassu-tip etc.

In one example, the tip may be made from one material injected by one of the first and second secondary melt channels and the rest of the catheter is made from another material injected by the other one of the first and second melt channels. In another example, the tip may be made from a material treated by one set of operation parameters, e.g. a first temperature and pressure, and injected by one of the first and second secondary melt channels, and the rest of the catheter is made from the same material treated by a another set of operation parameters, e.g. a second temperature and pressure, and injected by the other one of the first and second secondary melt channels. In this case, mixing of the melt outside the mould cavity would prevent the use of the first and second secondary melt channels to obtain different characteristics for different parts of the catheter.

The mould may be provided in two separate parts allowing the mould cavity to be divided into two cavity sections. This may particularly be along a dividing line allowing the moulded catheter to be removed from the mould cavity when the mould parts are separated. In this case, the first injection point may be in one of the two cavity sections, and the second injection point is in the other one of the two cavity sections. At the dividing line where the two cavity sections join, the mould may include a ventilation structure with a ventilation point in the mould cavity allowing release of air from the mould cavity. In this way, air may be released at a position between the first and second injection points and filing of melt into the mould from both the first and the second injection points is facilitated by one and the same ventilation structure. Also, the location of the ventilation point at the dividing line may support that the melt from the first and second secondary melt channels join at the dividing line which may be an advantage relative to removal of the moulded article from the mould. The ventilation structure may be controlled to provide a variable flow resistance, e.g. being varied depending on at least one of the temperature and pressure of the melt, e.g. in at least one of the first and the second secondary melt channels.

Within the meaning of this disclosure, the axial direction is defined by an axis extending along the centre of the catheter tube as seen on an unbent or undistorted catheter tube. The terms proximal and distal directions may be seen as in view of the user during insertion, i.e. the proximal end is the end closest to the user and the distal end faces away from the user. Furthermore, the term radial, radial axis or radial direction may be seen as a direction that is perpendicular to and intersects the axial direction of the catheter tube.

The first of the secondary melt channels may be provided to inject the melt into the mould cavity where the distal end of the urinary catheter is formed and the second of the secondary melt channels may be provided to inject the melt into the mould cavity where the tip of the urinary catheter is formed. In one embodiment, the first and second injection points point towards each other from opposite ends of the mould cavity, and in another embodiment, the first and second injection points point in the same direction, e.g. transversely or even perpendicularly into the axial direction of the catheter body. In one embodiment, the first and second injection points point in opposite directions, transverse or perpendicular to the axial direction and offset from each other in the axial direction. In another embodiment, the first and second injection points point towards each other in the axial direction.

The liquid catheter material to be injected may be a thermoplastic material. Suitable thermoplastic materials may be materials such as polyurethane, polyvinyl chloride, polyethylene and other thermo-formable materials.

Additionally, the catheter may comprise different materials for the tip, body, connector, or other distinct structures of the catheter. The catheter may e.g. have a surface layer making it slippery, e.g. a hydrophilic layer. The catheter may also have a connector made from a softer and more flexible material than the catheter tube, and the tip may be softer and more deflective and thus protect the mucous membrane during insertion. The different material combinations may be obtained e.g. by 2K-moulding where different materials are injected simultaneously or at different points in time into the same mould cavity, or it may be obtained by insert moulding where a tip, a connector, or other distinct structures are arranged in the mould cavity prior to the injection of moulding material therein.

On one embodiment, two different materials are injected from the first secondary melt channel and the second secondary melt channel. In one example, the catheter tube is formed by a first material injected by the first secondary melt channel and the connector, tip, or other distinct structures are formed by melt injected by the second secondary melt channel.

The mould may be provided with a core which forms the conduit extending in the body of the catheter, and the method may comprise the step of compressing the body in the axial direction until radial deformation of the body is obtained. This step may be carried out prior to a step of removing the catheter from the mould and particularly, it may be carried out to release the catheter from the core. By the compression of the body in axial direction, the catheter body and thus the conduit may be expanded in a direction perpendicular to the axial direction and by the increased internal size of the conduit, the core may easily slip out of the conduit. This procedure facilitates removal of the catheter from the mould cavity without destroying the core, and it therefore enables the use of longer, slimmer, and more fragile cores than typically used for injection moulding.

The removal of the catheter by axial compression may be carried out by pressing the aforementioned two separate parts of the mould cavity towards each other, e.g. by removal of an intermediate mould component located between the two separate mould parts during the injection of the melt into the mould cavity. Accordingly, the first and second injection points may be moved towards each other during the axial compression.

The melt may be injected from the first secondary melt channels such that it joins the melt from the second secondary melt channel at a transition being remote from a centre which is located halfway between the tip and the opening of the catheter. This particular location may be advantageous due to the typically increased size of the tip in a direction transverse to the axial direction compared to the transverse, radial, size of the rest of the catheter. By injection the melt such that it joins further towards the tip than towards the distal end, the increased size of the tip may be filled with increased efficiency and reduced risk of voids in the mould cavity. The transition may e.g. be in the range of 5-40 percent of the length from the tip to the opening away from the tip.

In a second aspect, an injection moulding apparatus is provided for injection moulding of a urinary catheter, the apparatus comprising a mould with a mould cavity forming a urinary catheter with an elongated body extending in an axial direction from a distal end to a proximal end and a tip terminating the catheter in the proximal end, and having a conduit extending in the body from an opening in the distal end to an opening in the tip;

a flow structure, e.g. a hot runner nozzle, for passing melt into the mould cavity, the flow structure comprising a primary melt channel in simultaneous communication with a first secondary melt channel and a second secondary melt channel, where the first secondary melt channel is connected to a first injection point of the mould cavity for injection of the melt into the mould cavity from the first injection point, and where the second secondary melt channel is connected to a second injection point of the mould cavity for injection of melt into the mould cavity from the second injection point, and a control structure configured to control the flow structures for injecting melt from the first and second secondary melt channels into the mould cavity simultaneously.

The control structure may comprise a first pressure control structure for setting a first pressure in the first secondary melt channel, and a second pressure control structure for setting a second pressure in the second secondary melt channel, the first pressure control structure being operable independent on the second pressure control structure. The pressure control structure may include a pump, e.g. a piston pump, e.g. a pump for each of the first and second secondary melt channels, and it may further comprise computer control means operably connected to the pump for controlling the flow and pressure from the pump.

At least one of the first and the second pressure control structures are configured for providing the first pressure or the second pressure such that it exceeds the pressure in the primary melt channel. The pressure control structure may e.g. be configured to provide a pressure in one or both of the secondary melt channels in the range of 2-10 times the pressure in the primary melt channel.

The control structure may comprise a first temperature control structure for setting a first temperature in the first secondary melt channel, and a second temperature control structure for setting a second temperature in the second secondary melt channel, the first temperature control structure being operable independent on the second temperature control structure.

The apparatus may comprise a sensor structure configured to provide a melt indicia based on at least one of the temperature, the viscosity, or the pressure of the melt and to communicate the melt indicia to the control structure. The control structure may include one or more sensors in the primary or secondary melt channels and/or in the mould cavity for obtaining temperature, viscosity, or pressure.

The control structure may be configured to control at least one of the pressure control structure and the temperature control structure based on the melt indicia, and the sensor structure may be configured to provide the melt indicia based on at least one of the temperature, the viscosity, or the pressure of the melt in the primary melt channel.

The sensor structure may be configured to provide the melt indicia based on at least one of the temperature, the viscosity, or the pressure of the melt in the mould cavity.

The apparatus may further comprise a servo system with at least a first and a second individual servo actuator for each of the first and second secondary melt channels. The first servo actuator could be configured to pressurise the melt in the first secondary melt channel and move the melt into the mould cavity, e.g. by movement of a first piston in a first cylinder, and the second servo actuator could be configured to pressurise the melt in the second secondary melt channel and move the melt into the mould cavity, e.g. by movement of a second piston in a second cylinder to thereby move the melt into the mould cavity.

The first and second piston may particularly move in a direction being transverse to, or even perpendicular to the axial direction.

The apparatus may further comprise a primary pressurising means configured to pressurise the melt in the primary melt channel, the primary pressurising means being configured to pressurise the melt independent on the pressure of the melt in the secondary melt channels. In one embodiment, the primary pressurising means is configured as a reciprocating screw mixer and it may include separate heating means capable of pre-heating the melt before it enters the first and second secondary melt channels. The primary pressuring means may be located offset in the axial direction relative to the mould. The primary pressuring means may also be located offset in the axial direction relative to the first and second pistons.

The apparatus may comprise memory means configured for storage of a control sequence defining at least one of a pressure and a temperature sequence defining pressure or temperature settings during injection of melt into the mould cavity and wherein the control structure is configured to control the pressure control structure or the temperature control structure based on a control sequence in the storage. The pressure and a temperature sequence may particularly define pressure or temperature settings individually for the first and second secondary melt channels and optionally also for the primary melt channel during injection of melt into the mould cavity.

The mould may comprise a core defining the conduit of the catheter, and the memory means may contain a control sequence defining a pressure sequence by which a radial pressure perpendicular to the axial direction is constant along the core during injection of melt into the mould cavity. The apparatus may include sensors capable of sensing deflection of the core, and to control the pressure and temperature of the melt in the first and or second secondary melt channel based on the measured deflection of the core.

The mould may comprise an intermediate mould component, first and second opposite outer components, and a core extraction system capable of:

moving the intermediate mould component away from the first and second opposite outer components, moving the first and second opposite outer components towards each other to expand a moulded catheter in a direction transverse to the axial direction, and removing the core while the component is expanded.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION OF THE DRAWINGS

Figure 1:
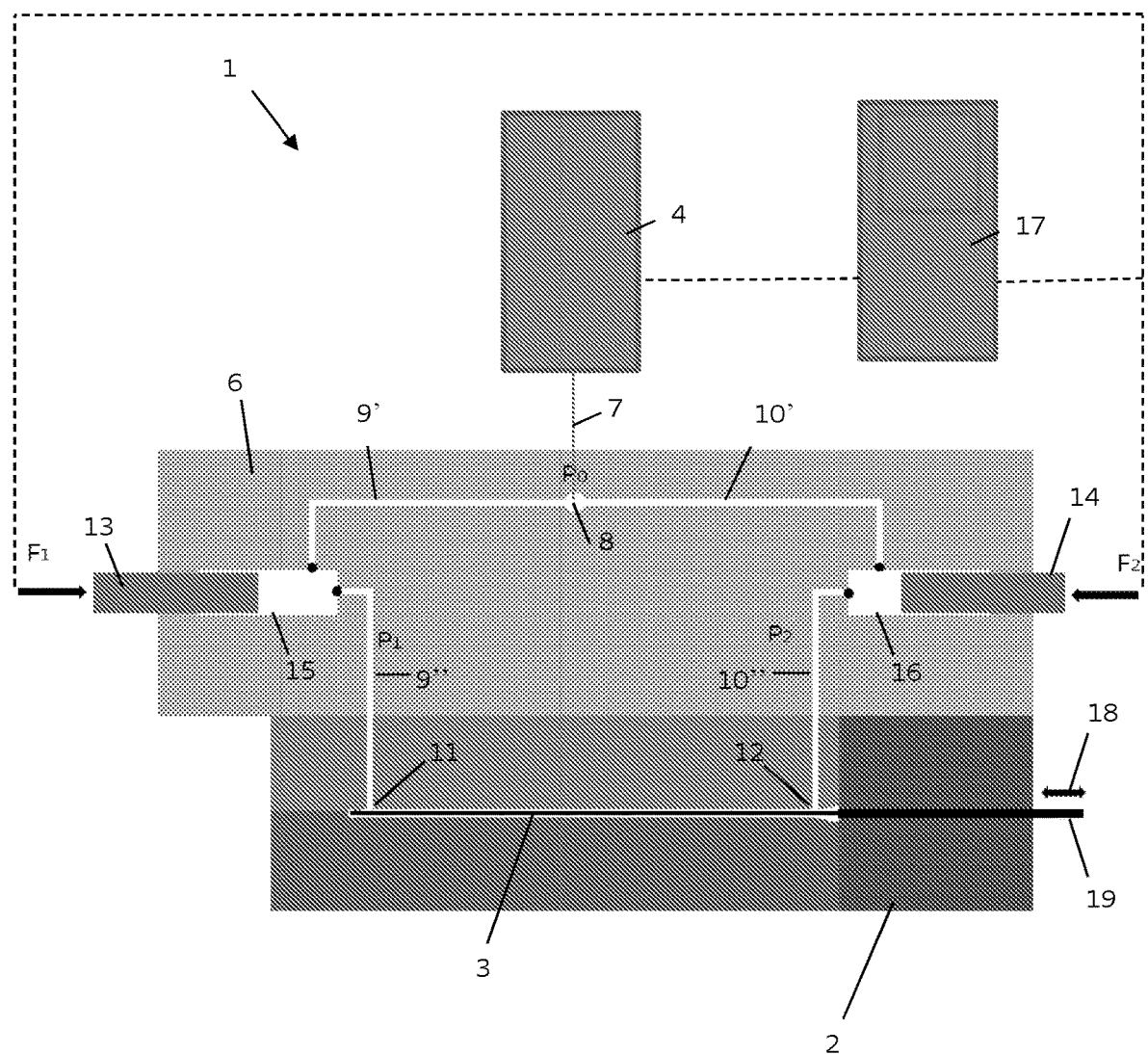
FIG. 1 illustrates a part of an injection moulding apparatus for moulding long and slim articles.

FIG. 1 illustrates an injection moulding apparatus 1 comprising a mould 2 with a mould cavity 3 forming a urinary catheter with an elongated body extending in an axial direction from a distal end to a proximal end and a tip terminating the catheter in the proximal end. The catheter defined by the mould cavity 3 has a conduit extending in the body from an opening in the distal end to an opening in the tip. The catheter thereby forms a traditional urinary catheter typically used e.g. for intermittent urinary catheterisation.

The conduit is formed during the moulding by an elongated and slim core extending through the mould cavity. To support the core and to prevent deformation or breaking of the core, the mould may include side elements (not shown). The side elements may extend transverse to the axial direction and engage the core to thereby support the core in the mould cavity.

The apparatus comprises a primary pressurising structure 4 only illustrated schematically by a box. The primary pressurising structure comprises a pressure piston and/or a worm including heating means. The apparatus further comprises a nozzle component 6 which is arranged to receive the melt from the primary pressurising structure via the primary melt channel 7.

The melt, which is pressurised by the primary pressurising structure, is moved through the primary melt channel 7 to a manifold junction 8 in the nozzle component.

In the nozzle component, the melt splits into a first secondary melt channel 9', 9" and a second secondary melt channel 10', 10". Via the manifold junction 8, the primary melt channel 7 is in simultaneous communication with both the first secondary melt channel and the second secondary melt channel.

The first secondary melt channel is connected to a first injection point 11 of the mould cavity for injection of the melt into the mould cavity from the first injection point. The second secondary melt channel is connected to a second injection point 12 of the mould cavity for injection of melt into the mould cavity from the second injection point.

The secondary melt channels are connected to the two different injection points 11, 12 of the mould cavity and thereby enable injection of melt into the mould cavity from different positions. In the illustration, the injection points are in opposite ends of the elongate catheter shape.

Each of the first and second secondary melt channels 9',9",10',10" comprises a pressure control structure, in the illustrated embodiment being in the form of pistons 13, 14, movable in cylinders 15, 16. The pressure control structure is capable of pressuring the melt individually in each of the first and second secondary melt channels. The illustrated forces F1, F2 applied individually to each of the pistons can be provided by servo motors.

The apparatus comprises a computer control 17 which is connected to the servo structure illustrated by the forces F1 and F2. The computer control 17 is further connected to the primary pressurising structure 4 and thereby controls pressurisation of the melt.

The computer control 17 is further connected to heaters (not shown) which can adjust the temperature in at least one of the first and second secondary melt channel. The heaters are individual heaters capable of setting individual temperatures in the first and second secondary melt channels.

The computer control 17 is further connected to sensors (not illustrated) which can sense the temperature and to sensors (not shown) which can determine the viscosity of the melt.

The viscosity may also be determined by the computer control based on materiel properties and temperature and/or pressure.

The apparatus comprises a core extraction structure 18 configured to arrange a core 19 in the mould cavity, and configured to remove the core once a catheter is moulded. The core extraction structure is configured to effect an axial compression of the moulded article and thereby a radial expansion of the conduit formed by the core. In that way, the core can be released from the conduit walls and removed more easily.

Figure 2:
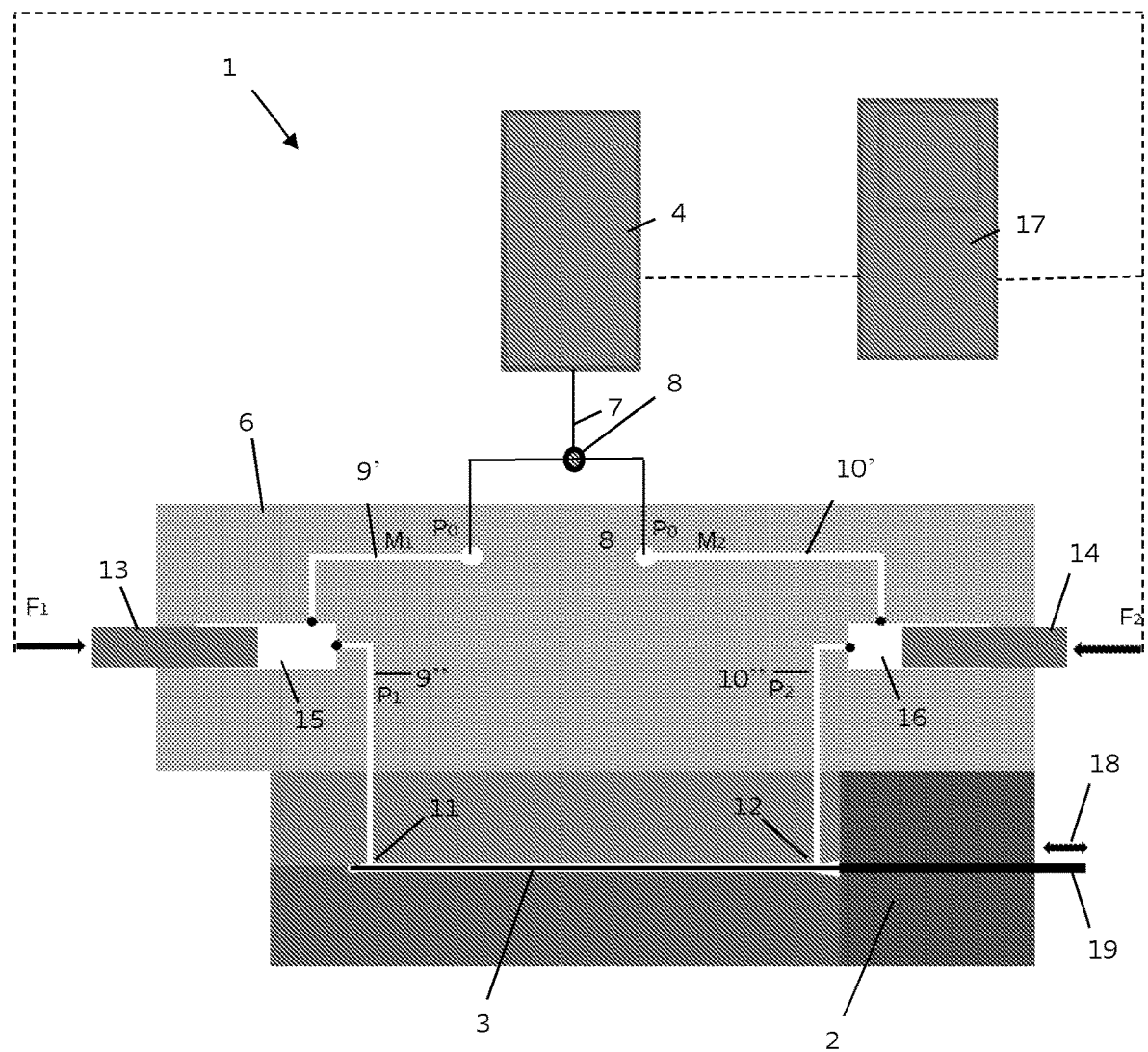
FIG. 2 illustrates a part of an alternative injection moulding apparatus for moulding long and slim articles.

FIG. 2 illustrates an embodiment where the nozzle component 6 receives the melt from the primary melt channel 7 via a manifold junction 8 being external to the nozzle unit.

In the embodiments of FIGS. 1 and 2, the melt from the first secondary melt channel and the second secondary melt channel are injected individually at the first and second injection points and the melt is not joined until the two separate flows of melt from the first and second injection points meet inside the mould cavity.

The invention claimed is:

1. A method of forming a urinary catheter, the method comprising:
providing a mould having a mould cavity forming an elongated recess extending in an axial direction from a distal end of the recess to a tip terminating at a proximal end of the recess;
providing a core inserted into the elongated recess of the mould cavity;
coupling a flow structure to the mould, with the flow structure comprising a primary melt channel in simultaneous communication with a first secondary melt channel and a second secondary melt channel;
coupling the first secondary melt channel to a first injection location of the mould cavity and coupling the second secondary melt channel to a second injection location of the mould cavity;
injecting a polymer melt through the primary melt channel and into the elongated recess around an outer surface of the core;
controlling a first pressure of the polymer melt in the first secondary melt channel separately and individually from a second pressure of the polymer melt in the second secondary melt channel and reducing stress of the polymer melt along the elongated recess; and opening the mould, removing the core, and providing a moulded intermittent urinary catheter having an open distal end and a closed proximal tip.

2. The method of claim 1, further comprising:
controlling a first temperature of the polymer melt in the first secondary melt channel separately and individually from a second temperature of the polymer melt in the second secondary melt channel.

3. The method of claim 2, further comprising:
coupling the first secondary melt channel to the first injection location of the mould cavity and coupling the second secondary melt channel to the second injection location of the mould cavity, and injecting the polymer melt through the primary melt channel such that the polymer melt from the first secondary melt channel meets the polymer melt from the second secondary melt channel at a midpoint of the elongated recess.

4. The method of claim 2, further comprising:
coupling the first secondary melt channel to the first injection location of the mould cavity and coupling the second secondary melt channel to the second injection location of the mould cavity, and injecting the polymer melt through the primary melt channel such that the polymer melt from the first secondary melt channel meets the polymer melt from the second secondary melt channel at an offset location closer to the proximal end of the recess than to the distal end of the recess.

5. The method of claim 2, further comprising:
providing the moulded intermittent urinary catheter having a larger tip diameter at the closed proximal tip compared to a diameter measured at the open distal end of the moulded intermittent urinary catheter by steps including:
injecting the polymer melt through the primary melt channel and controlling the first pressure of the polymer melt in the first secondary melt channel separately and individually from the second pressure of the polymer melt in the second secondary melt channel such that the polymer melt from the first secondary melt channel meets the polymer melt from the second secondary melt channel at an offset location closer to the proximal end of the recess than to the distal end of the recess.

6. The method of claim 2, further comprising:
simultaneously injecting the polymer melt in the first secondary melt channel and the second secondary melt channel and providing a homogeneous pressure distribution in the elongated recess around the outer surface of the core.

7. The method of claim 2, further comprising:
injecting a first polymer melt in the first secondary melt channel and a second polymer melt in the second secondary melt channel, with the second polymer melt having a different material than the first polymer melt.

8. The method of claim 2, further comprising:
controlling the first pressure of the polymer melt in the first secondary melt channel and the second pressure of the polymer melt in the second secondary melt channel such that a pressure in the primary melt channel is less than at least one of the first pressure and the second pressure.

9. The method of claim 2, further comprising:
controlling one of the first pressure of the polymer melt in the first secondary melt channel and the second pressure of the polymer melt in the second secondary melt channel based on a static pressure measurement without reference to a pressure in the mould cavity.

10. The method of claim 2, further comprising:
coupling the first secondary melt channel to the distal end of the recess and coupling the second secondary melt channel to the proximal end of the recess.

11. The method of claim 2, further comprising:
opening the mould, axially compressing the moulded intermittent urinary catheter, and removing the core.

\* \* \* \* \*